(12) United States Patent
Chen et al.

(10) Patent No.: US 10,962,482 B2
(45) Date of Patent: Mar. 30, 2021

(54) SURFACE ENHANCED RAMAN SCATTERING DEVICE AND METHOD OF MANUFACTURING THE SAME

(71) Applicant: NATIONAL TSING HUA UNIVERSITY, Hsinchu (TW)

(72) Inventors: yu-hsuan Chen, Hsinchu (TW); Hsuen-Li Chen, Hsinchu (TW); De-hui Wan, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 16/533,787

(22) Filed: Aug. 7, 2019

(65) Prior Publication Data
US 2020/0371035 A1    Nov. 26, 2020

(30) Foreign Application Priority Data
May 20, 2019 (TW) .................. 108117250

(51) Int. Cl.
*G01N 21/65* (2006.01)
*G01J 3/44* (2006.01)
*G01N 33/58* (2006.01)

(52) U.S. Cl.
CPC .............. *G01N 21/658* (2013.01); *G01J 3/44* (2013.01); *G01N 33/587* (2013.01)

(58) Field of Classification Search
CPC .................................................. G01N 21/658
USPC .......................................................... 356/301
See application file for complete search history.

(56) References Cited

U.S. PATENT DOCUMENTS

| 10,060,904 B1* | 8/2018 | Brueck ............. G01N 33/48721 |
| 2010/0003316 A1* | 1/2010 | Vo Dinh ............. A61K 41/0066 514/1.1 |
| 2011/0267609 A1* | 11/2011 | Wu ....................... G01N 21/658 356/301 |
| 2012/0081703 A1* | 4/2012 | Moskovits ........... G01N 21/658 356/301 |
| 2012/0287427 A1* | 11/2012 | Li ......................... B82Y 20/00 356/301 |
| 2017/0261434 A1* | 9/2017 | Gwo ...................... G01N 21/658 |
| 2018/0231418 A1* | 8/2018 | Park ..................... C23C 16/0236 |

FOREIGN PATENT DOCUMENTS

WO    WO-2008063136 A1 *    5/2008    ............... G01N 1/31

* cited by examiner

*Primary Examiner* — Tarifur R Chowdhury
*Assistant Examiner* — Omar H Nixon
(74) *Attorney, Agent, or Firm* — Chun-Ming Shih; Lanway IPR Services (57) ABSTRACT

A surface enhanced Raman scattering device includes a substrate including a substrate surface having a substrate surface energy; a modulation layer formed on the substrate surface and including a modulation layer surface having a modulation layer surface energy; and a surface enhanced Raman scattering structure formed on the modulation layer surface. The modulation layer surface energy is less than the substrate surface energy. A method of manufacturing the surface enhanced Raman scattering device is also provided.

17 Claims, 8 Drawing Sheets

SURFACE ENHANCED RAMAN SCATTERING DEVICE AND METHOD OF MANUFACTURING THE SAME

BACKGROUND OF THE INVENTION

1. Technical Field

The technical field relates to scattering devices and methods of manufacturing the same, and more particularly relates to a surface enhanced Raman scattering device for detecting subjects having a smaller amount and method of manufacturing the same being characterized by high sensitivity and having wide applications in food safety check, environmental pollution prevention and clinical testing.

2. Description of Related Art

Health and safety are big issues in our society. For example, drug abuse, food safety, and biological molecules testing for diseases are great concerns. Typically, testing methods are time consuming and/or labor intensive. It is impossible of determining an item being tested is drug or not at the time of testing. Further, the test result may be pseudo positive due to food eaten by an employee or medicinal interference. Furthermore, its cost is very high. Thus, attentions paid to the surface enhanced Raman scattering are more than most effective testing methods. Advantages of the surface enhanced Raman spectrum include real time testing, having a specific fingerprint spectrum for different molecules so as to analyze known or unknown molecular structure of a subject, and being used for identifying the subject.

Raman test takes metal nanostructures having an enhanced electromagnetic effect as a substrate. In disclosed documents, methods including chemically changing particles sizes and orientations, using functional bases to modify the substrate, photolithography and electron beam lithography are used to control surface plasma resonance frequencies of a metal and its resonance strength. However, the conventional methods are disadvantageous due to complicated manufacturing steps and extremely high cost of required high precision apparatuses.

Thus, it is desired by the invention to provide a surface enhanced Raman scattering device and a method of manufacturing same having simple substrate, manufacturing steps and greatly decreased cost.

SUMMARY OF THE INVENTION

The disclosure is directed to a surface enhanced Raman scattering device and a method of manufacturing same for eliminating drawbacks including those associated with the conventional art.

It is therefore one object of the invention to provide a surface enhanced Raman scattering device, comprising a substrate including a substrate surface having a substrate surface energy; a modulation layer formed on the substrate surface and including a modulation layer surface having a modulation layer surface energy; and a surface enhanced Raman scattering structure formed on the modulation layer surface wherein the modulation layer surface energy is less than the substrate surface energy.

One of the exemplary embodiments, the surface enhanced Raman scattering structure includes a plurality of discontinuously, densely arranged metal nanoparticles.

One of the exemplary embodiments, the surface enhanced Raman scattering structure includes a plurality of local electric field gain zones, the local electric field gain zones being on the modulation layer surface.

One of the exemplary embodiments, local electric field gains of the local electric field gain zones are not the same.

One of the exemplary embodiments, attraction force among metal atoms of the metal nanoparticles is greater than that between the metal nanoparticles and the modulation layer surface.

One of the exemplary embodiments, there is further provided a subject solution including a plurality of subjects and a solvent, the subject solution being on both the modulation layer surface and the surface enhanced Raman scattering structure, and wherein attraction force among molecules of the solvent is greater than that between the solvent and the modulation layer surface.

One of the exemplary embodiments, there is further provided a plurality of subjects in the local electric field gain zones.

It is another object of the invention to provide a surface enhanced Raman scattering device, comprising a substrate including a substrate surface having a substrate surface energy; a modulation layer formed on the substrate surface and including a modulation layer surface having a modulation layer surface energy wherein the modulation layer surface energy is less than the substrate surface energy; and a synthesized solution on the modulation layer surface, the synthesized solution including a plurality of subjects, a solvent, and a plurality of metal nanoparticles wherein attraction force among molecules of the solvent is greater than that between the solvent and the modulation layer surface.

It is still another object of the invention to provide a method of manufacturing a surface enhanced Raman scattering device, comprising the steps of providing a substrate including a substrate surface having a substrate surface energy; and forming a modulation layer on the substrate surface for decreasing the substrate surface energy, the modulation layer including a modulation layer surface having a modulation layer surface energy wherein the modulation layer surface energy is less that the substrate surface energy.

One of the exemplary embodiments, the modulation layer is formed on the substrate surface by means of vapor deposition.

One of the exemplary embodiments, there is further provided the step of forming a surface enhanced Raman scattering structure on the modulation layer surface by sputtering, the surface enhanced Raman scattering structure including a plurality of discontinuously, densely arranged metal nanoparticles which form a plurality of local electric field gain zones.

One of the exemplary embodiments, there is further provided the step of forming a surface enhanced Raman scattering structure on the modulation layer surface by coating a solution having a plurality of dispersed metal nanoparticles on the modulation layer surface, the surface enhanced Raman scattering structure including a plurality of discontinuously, densely arranged metal nanoparticles which form a plurality of local electric field gain zones.

One of the exemplary embodiments, the metal nanoparticles include a metal precursor and a reducing agent.

One of the exemplary embodiments, there are further provided the steps of providing a subject solution including a plurality of subjects and a solvent, coating the subject solution on both the surface enhanced Raman scattering structure and the modulation layer surface, and evaporating the solvent to leave the subjects in the local electric field gain zones.

One of the exemplary embodiments, there are further provided the steps of providing a synthesized solution including a plurality of subjects, a solvent, and a plurality of metal nanoparticles, coating the synthesized solution on the modulation layer surface, and concentrating the metal nanoparticles to form a surface enhanced Raman scattering structure by evaporating the solvent wherein the surface enhanced Raman scattering structure includes a plurality of discontinuously, densely arranged metal nanoparticles which form a plurality of local electric field gain zones, and the subjects are in the local electric field gain zones.

The above and other objects, features and advantages of the invention will become apparent from the following detailed description taken with the accompanying drawings.

DETAILED DESCRIPTION OF THE INVENTION

Embodiments of the invention will now be described, by way of example only, with reference to the accompanying drawings.

Figure 1:
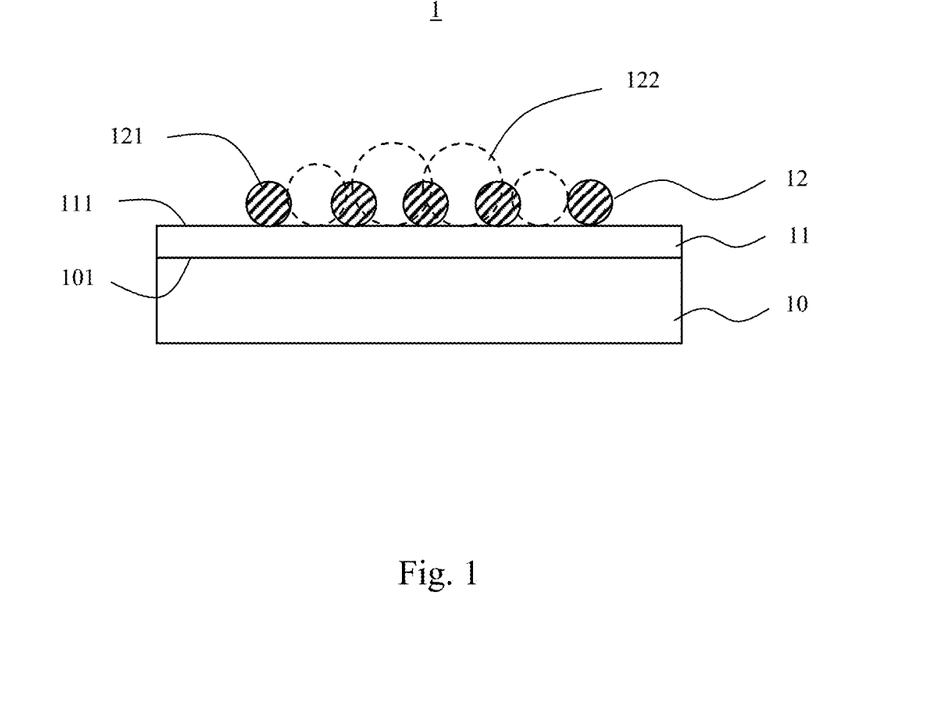
FIG. 1 schematically depicts a surface enhanced Raman scattering device according to a first preferred embodiment of the invention.

Referring to FIG. 1, a surface enhanced Raman scattering device 1 in accordance with a first preferred embodiment of the invention is shown. The surface enhanced Raman scattering device 1 comprises a substrate 10 including a substrate surface 101 having a substrate surface energy; a modulation layer 11 formed on the substrate surface 101 and including a modulation layer surface 111 having a modulation layer surface energy in which the modulation layer surface energy is less than the substrate surface energy; and a surface enhanced Raman scattering structure 12 formed on the modulation layer surface 111.

The substrate 10 comprises semiconductor materials including $MoS_2$, Si wafer, and Ge wafer in a non-limiting manner; oxide materials including $SiO_2$, ZnO, ITO, and AAO in a non-limiting manner; plants and animals materials including rose, marguerite, peach blossoms, pineapple, clam shell, fish scale, egg shell in a non-limiting manner; porous materials or sponges including polyurethane (PU) sponge, polyester (PE) sponge, polyvinyl alcohol (PVA) sponge, natural pulp, synthetic rubber, Ni foam, Melamine form (formaldehyde-melamine-sodium bisulfite copolymer) sponge, PVDF filter membrane, PTFE membranes in a non-limiting manner; flexible materials including paper, silk fabrics, cotton fabrics in a non-limiting manner; macromolecular materials including PVA Polyvinyl alcohol, PVC Polyvinyl Chloride, PAN Polyacrylonitrile, PMMA Poly (methyl methacrylate), PET Polyethylene terephthalate, PDMS Polydimethylsiloxane, PC Polycarbonate/Optical Disc, PS Polystyrene, PLA Polylactic Acid, Hydroxyethyl cellulose, chitin nanopillar arrays in a non-limiting manner; metal materials including aluminum, gold, silver, copper, iron, nickel, cobalt, titanium, alloy in a non-limiting manner; Nano/micro particle including Al nanocrystals, Al nanohole arrays, Au nanorods, Au nanostars, polyhedral Au nanoparticles, Au nanorattles, Au nanosphere, Au nanoflowers, Au nanoshells, Au nanobipyramids, Ag nanoplates, Ag nanocubes, Ag nanotriangles, core-shell nanoparticles in a non-limiting manner; Nanowires including Copper nanowires, Silicon nanowires, Silver nanowires in a non-limiting manner; and Carbon nanomaterials including Carbon Nanotube CNT, Graphene, Graphene oxides, Graphitic carbon nitride in a non-limiting manner.

The modulation layer 11 is provided to form the modulation layer surface 111 having a modulation layer surface energy which is less than the substrate surface energy. The lower surface energy results in superhydrophobic condensation effect. When a subject solution falls on the modulation layer surface 111 having lower surface energy, the spatial distribution range of subject can be decreased to a minimum as the solvent evaporates. Thus, only a smaller amount of subject is need to achieve stronger Raman measurement signals and the purpose of testing a trivial subject. The invention employs the modulation layer 11 to change the substrate surface energy of the substrate surface 101 in order to form the modulation layer surface 111 having a smaller surface energy. Therefore, it is possible of manufacturing highly sensitive Raman measurement for subjects having a smaller amount. Also, it is applicable to a surface enhanced Raman scattering substrate for practical testing or clinical testing.

The purpose of the modulation layer 11 is to form the modulation layer surface 111 having a lower surface energy. Materials of the modulation layer 11 can be 1H, 1H, 2H, 2H-perfluorooctyl trichloro silane (PFOTS), 1H,1H,2H,2H-Perfluorooctyltriethoxysilane (POTS), 1H,1H,2H,2H-perfluorodecyltrichlorosilane (FDDTS), 1H,1H,2H,2H-Perfluorodecyltriethoxysilane (PFDTES), 1H,1H,2H,2H-Perfluorodecyltrimethoxysilane, (Heptafluoropropyl)trimethylsilane, Trichloro(3,3,3-trifluoropropyl)silane, Trichloro(phenethyl)silane, Trimethoxymethylsilane, Trimethoxy(3,3,3-trifluoropropyl)silane, Tris(dimethylamino)chlorosilane, Chloro-dimethyl(3,3,3-trifluoropropyl)silane, Chloro(dodecyl)dimethylsilane, Chloro(dimethyl)octylsilane, Chloro(dimethyl)isopropylsilane, Chlorodimethyl(pentafluorophenyl)silane, Chlorodimethylphenethylsilane, Chloro(methyl)phenylsilane, Chloro(methyl)diphenylsilane, (Chloromethyl)methyibis(pentafluorophenyl)silane, Chlorodiethylisopropylsilane, Chlorotriisobutylsilane, Chlorotriethylsilane, Chlorotripropylsilane, Chloro-decyldimethylsilane, Triisopropylsilyl chloride, Dimethoxymethyl(3,3,3-trifluoropropyl)silane, Dimethylisopropylsilane, Butyl(chloro)dimethylsilane, Benzylchlorodimethylsilane, Polyvinyl Alcohol (PVA) liquid, chlorinated hydrocarbons, chloro-fluorocarbons, fluorocarbon materials: perfluorooctanoic acid (PFOA) in a non-limiting manner as long as it forms the modulation layer surface energy less than the substrate surface energy and is within the scope of the invention.

In the embodiment, the surface enhanced Raman scattering device 1 further comprises a surface enhanced Raman scattering structure 12 formed on the modulation layer surface 111. The surface enhanced Raman scattering structure 12 includes a plurality of discontinuously, densely arranged metal nanoparticles 121 which include one or more metal materials as constituents. It is understood that in other embodiments the following are within the scope of the invention: forming a metal nanostructure having a surface enhanced Raman scattering effect on the modulation layer surface 111, and using localized surface plasma resonance (LSPR) of the metal nanostructure to form a local electric field gain zone. Materials of the metal nanoparticles 121 are nanoscale metal materials including aluminum, gold, silver, copper, iron, nickel, cobalt, titanium, platinum, chromium, and alloy capable of having a surface enhanced Raman scattering effect. The metal nanostructure includes, but not limited to, nanoscale metal particles, nanoscale metal posts, nanoscale metal bars, nanoscale metal threads, nanoscale metal cubes, and nanoscale metal discs. The metal nanostructure includes a combination consisting of one or more of above identified members having different structures.

As shown in FIG. 1, on the modulation layer surface 111 there is a surface enhanced Raman scattering structure 12 including a plurality of discontinuously, densely arranged metal nanoparticles 121, and a plurality of local electric field gain zones 122 among the plurality of metal nanoparticles 121 in which the local electric field gain zones 122 are on the modulation layer surface 111. Geometric shapes and sizes of the metal nanoparticles 121 affect the resonance frequency and intensity. Also, gap distance between any two metal nanoparticles 121 affects the resonance frequency and intensity. In the embodiment, the local electric field gains of the local electric field gain zones 122 are not the same. It is understood that gap distance between any two of the discontinuously, densely arranged metal nanoparticles 121 are the same or different. But they are within the scope of the invention as long as they can form the local electric field gain zones 122.

Figure 2:
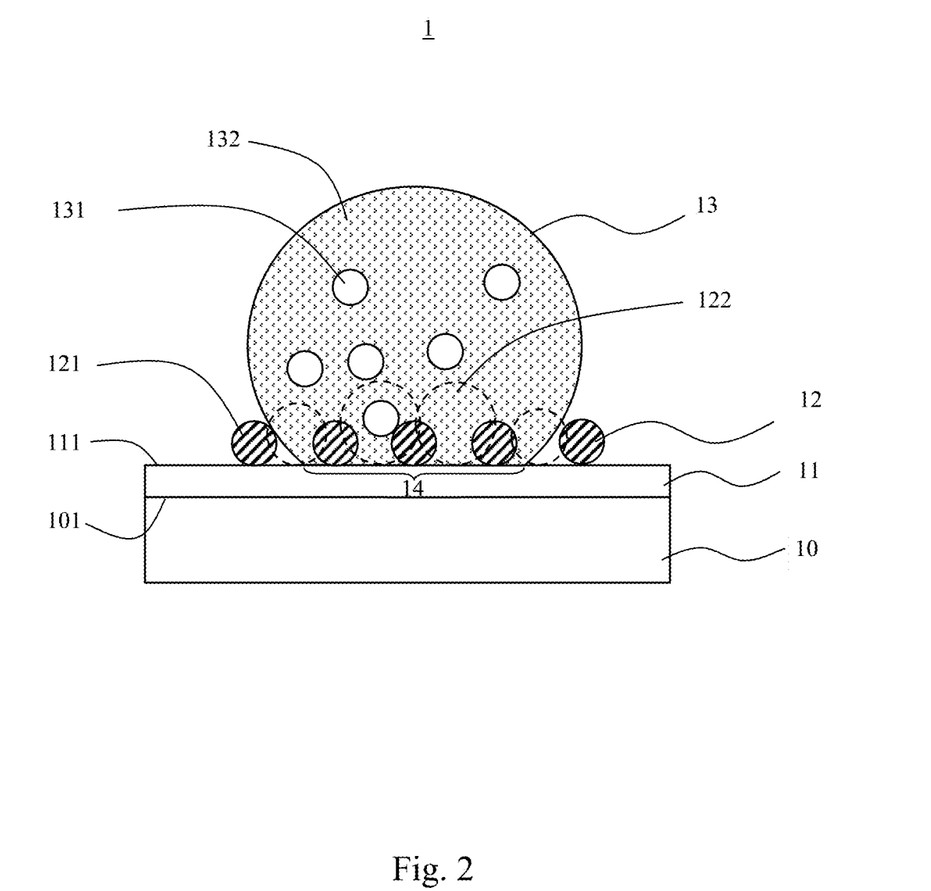
FIG. 2 schematically depicts the surface enhanced Raman scattering device including the subject solution.
Figure 3:
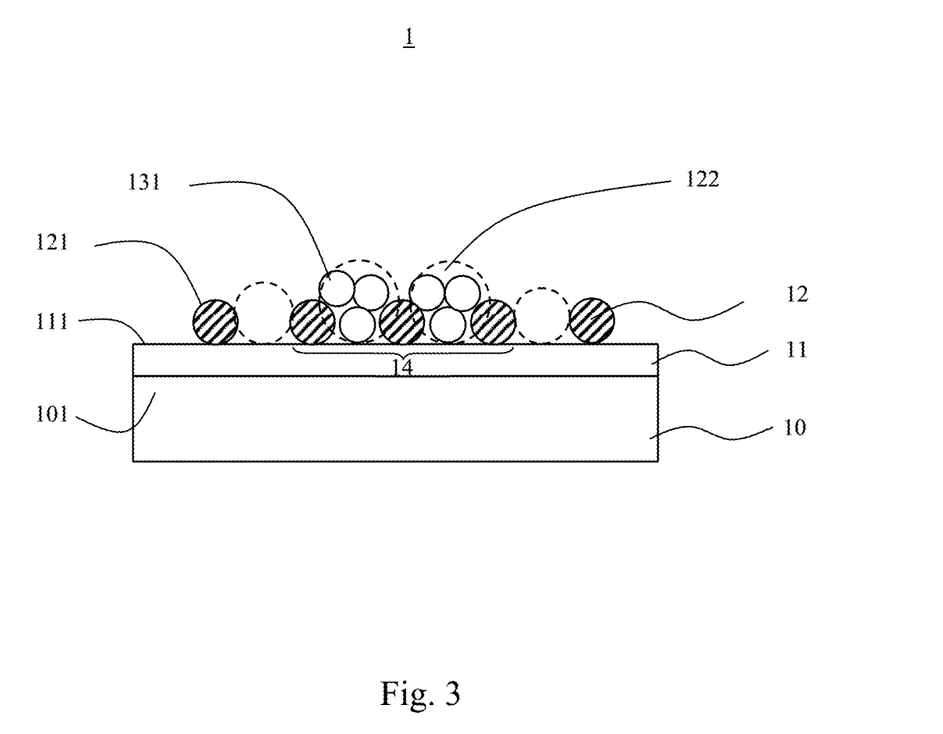
FIG. 3 schematically depicts the surface enhanced Raman scattering device of FIG. 2, and the subjects being in local electric field gain zones after the solvent has evaporated.

Referring to FIGS. 2 and 3, it shows the surface enhanced Raman scattering device 1 of the first preferred embodiment of the invention of FIG. 1. The surface enhanced Raman scattering device 1 comprises a subject solution 13 on both the modulation layer surface 111 and the surface enhanced Raman scattering structure 12. A hydrophobic region is formed between the subject solution 13 and the modulation layer surface 111 due to less surface energy of the modulation layer surface 111. A condensation zone 14 is formed between the substrate surface 101 and the subjects 131. The condensation zone 14 includes a portion of the modulation layer surface 111 and a portion of the surface enhanced Raman scattering structure 12. Attraction force among molecules of the solvent 132 is greater than that between the solvent 132 and the modulation layer surface 111. Attraction force among metal atoms of the metal nanoparticles 121 is greater than that between the metal nanoparticles 121 and the modulation layer surface 111.

As shown FIG. 3 specifically, it shows the subjects 131 being in the local electric field gain zones 122 after the solvent 132 has evaporated. In the embodiment, attraction force among molecules of the solvent 132 is greater than that between the solvent 132 and the modulation layer surface 111. The subjects 131 are in the condensation zone 14, particularly in the local electric field gain zones 122 in the condensation zone 14 after the solvent 132 has evaporated. In the embodiment, the metal nanoparticles 121, the local electric field gain zones 122 and the subjects 131 are on the modulation layer surface 111.

Figure 4:
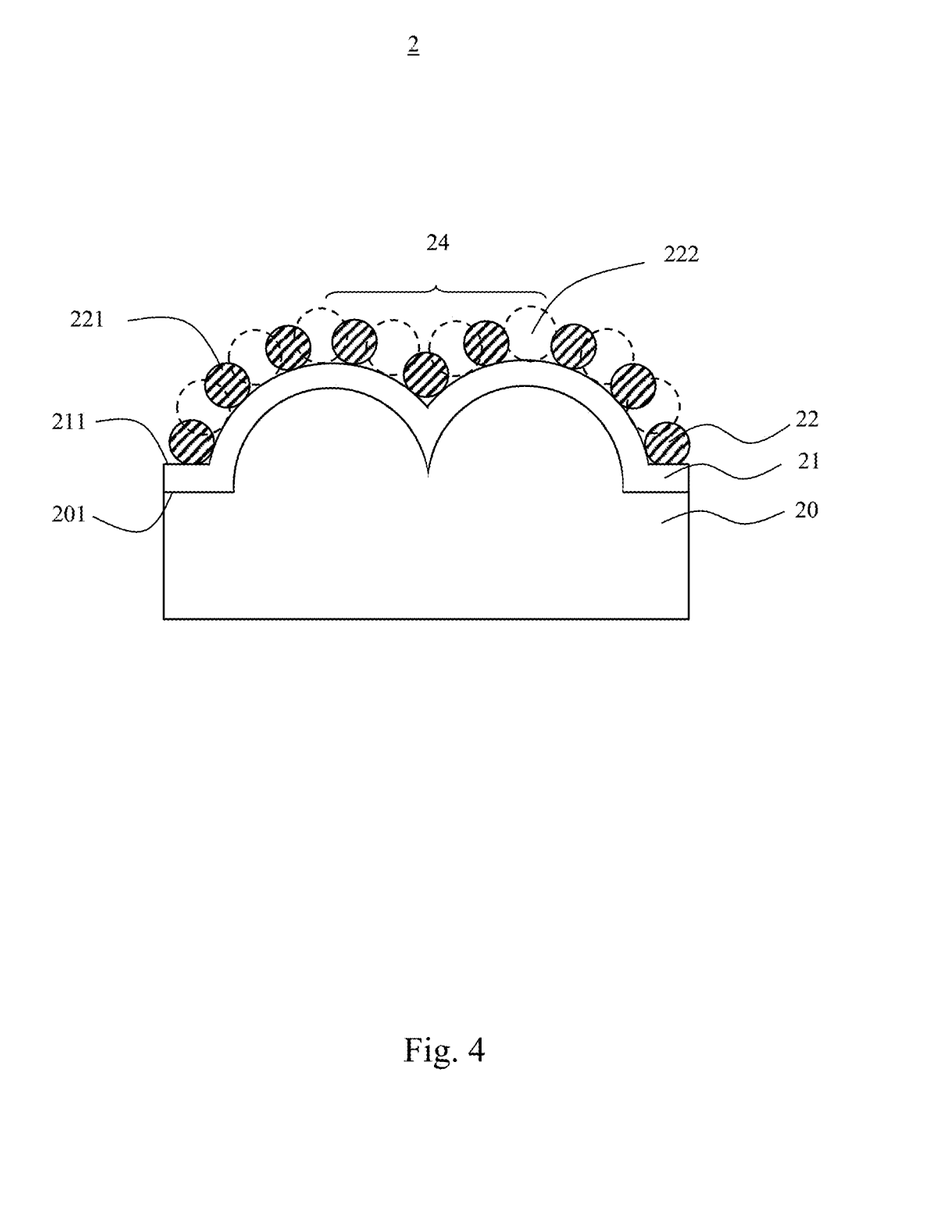
FIG. 4 schematically depicts a surface enhanced Raman scattering device according to a second preferred embodiment of the invention.

Referring to FIG. 4, a surface enhanced Raman scattering device 2 in accordance with a second preferred embodiment of the invention is shown. The surface enhanced Raman scattering device 2 comprises a substrate 20 including a substrate surface 201 having a substrate surface energy; a modulation layer 21 formed on the substrate surface 201 and including a modulation layer surface 211 having a modulation layer surface energy in which the modulation layer surface energy is lessthan the substrate surface energy; and a surface enhanced Raman scattering structure 22 formed on the modulation layer surface 211. The surface enhanced Raman scattering structure 22 includes a plurality of discontinuously, densely arranged metal nanoparticles 221 which include one or more metal materials as constituents. The second preferred embodiment is different from the first preferred embodiment by the following: The substrate surface 201 of the substrate 20 is a three-dimensional structure such as a rough surface so as to increase density of the metal nanoparticles 221 in the three-dimensional space. In the depth of focus, there are provided more local electric field gain zones 222 and molecules of a subject, thereby enhancing Raman scattering effect. As shown in FIG. 4, the modulation layer surface 211 is formed on the substrate surface 201 and the modulation layer 211 is shaped as shape of the top of the substrate surface 201 changes.

Figure 5:
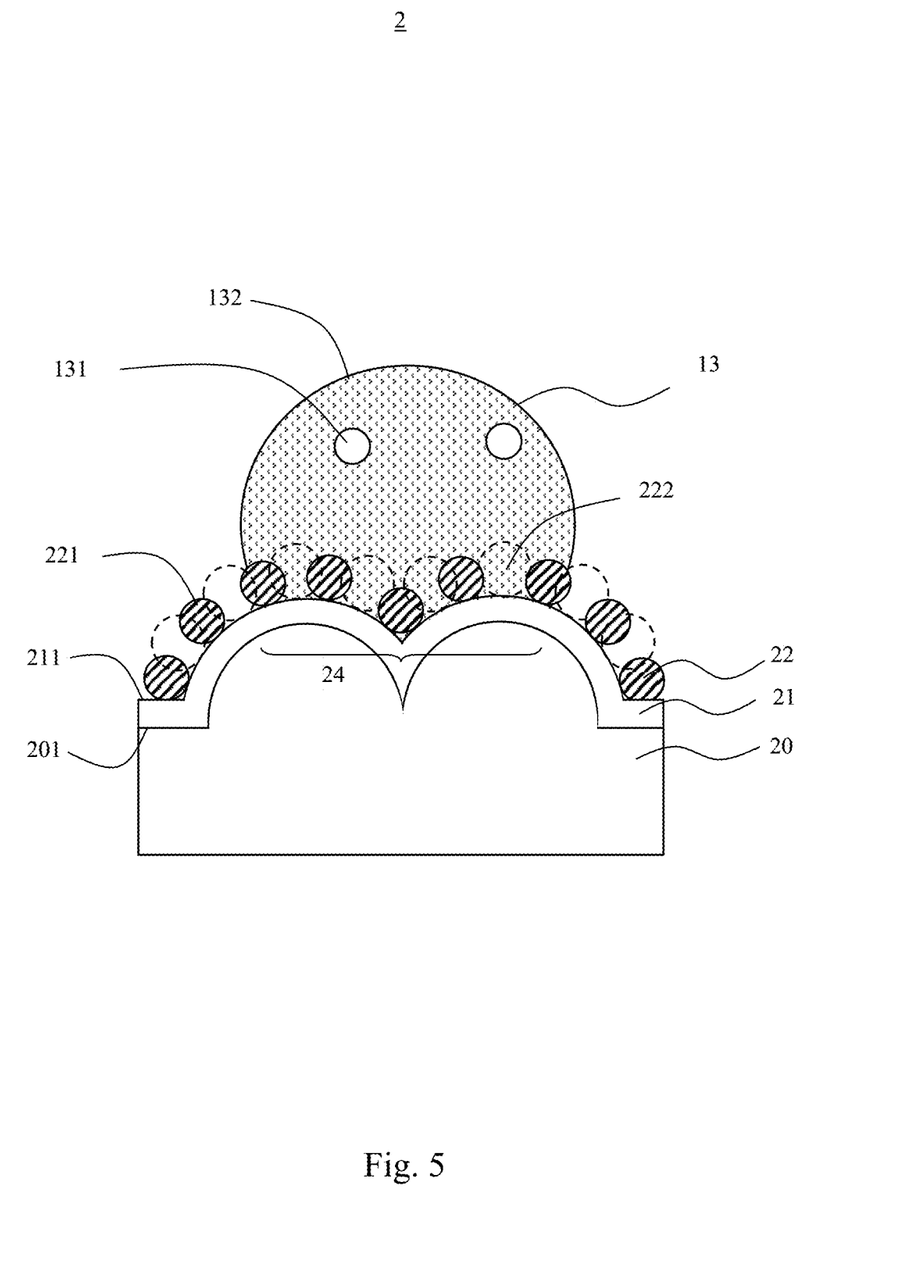
FIG. 5 schematically depicts the surface enhanced Raman scattering device including the subject solution of FIG. 4.

Referring to FIG. 5, it shows the subject solution 13 disposed on both the modulation layer surface 211 and the surface enhanced Raman scattering structure 22. A hydrophobic region is formed between the subject solution 13 and the modulation layer surface 211 due to lesssurface energy of the modulation layer surface 211. A condensation zone 24 is formed on the modulation layer surface 211 which contacts the subject solution 13. Attraction force among molecules of the solvent 132 is greater than that between the solvent 132 and the modulation layer surface 211. The subjects 131 concentrate in the condensation zone 24, particularly in the local electric field gain zones 222 after the solvent 132 has evaporated. It is understood that the condensation zone 24 is located at a convex portion, a concave portion, or convex and concave portions of the three-dimensional structure and these are within the scope and spirit of the invention.

Figure 6:
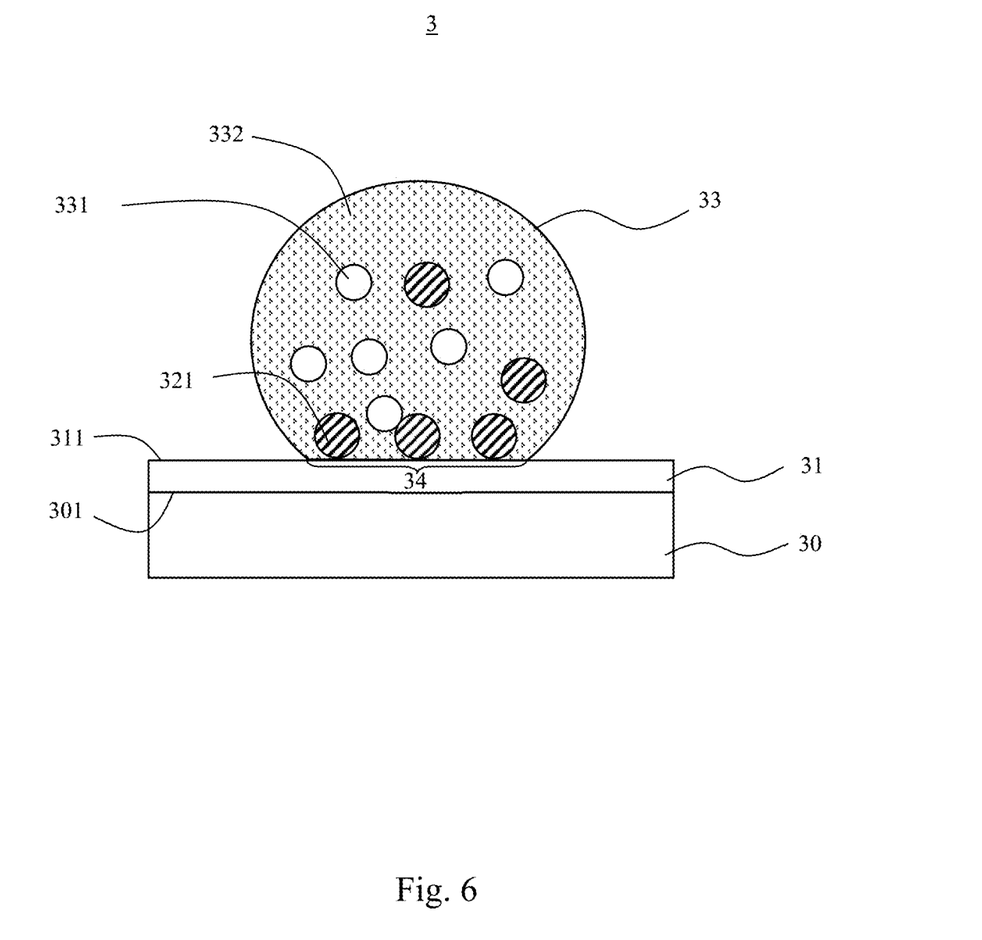
FIG. 6 schematically depicts a surface enhanced Raman scattering device according to a third preferred embodiment of the invention, and the synthesized solution.

Referring to FIG. 6, a surface enhanced Raman scattering device 3 according to a third preferred embodiment of the invention is shown. The surface enhanced Raman scattering device 3 comprises a substrate 30 including a substrate surface 301 having a substrate surface energy; a modulation layer 31 formed on the substrate surface 301 and including a modulation layer surface 311 having a modulation layer surface energy in which the modulation layer surface energy is less than the substrate surface energy; and a synthesized solution 33 on the modulation layer surface 311. The synthesized solution 33 includes a plurality of subjects 331, a solvent 332, and a plurality of metal nanoparticles 321 in which attraction force among molecules of the solvent 332 is greater than that between the solvent 332 and the modulation layer surface 311, and attraction force among metal atoms of the metal nanoparticles 321 is greater than that between the metal nanoparticles 321 and the modulation layer surface 111. The metal nanoparticles 321 are formed of a single kind of metal or different kinds of metal. Both the subjects 331 and the metal nanoparticles 321 concentrate in the condensation zone 34 after the solvent 332 has evaporated. A surface enhanced Raman scattering structure (not shown) is formed on the modulation layer surface 311 by the metal nanoparticles 321. Also, the subjects 331 are formed in the local electric field gain zones (not shown) on the surface enhanced Raman scattering structure.

Figure 7:
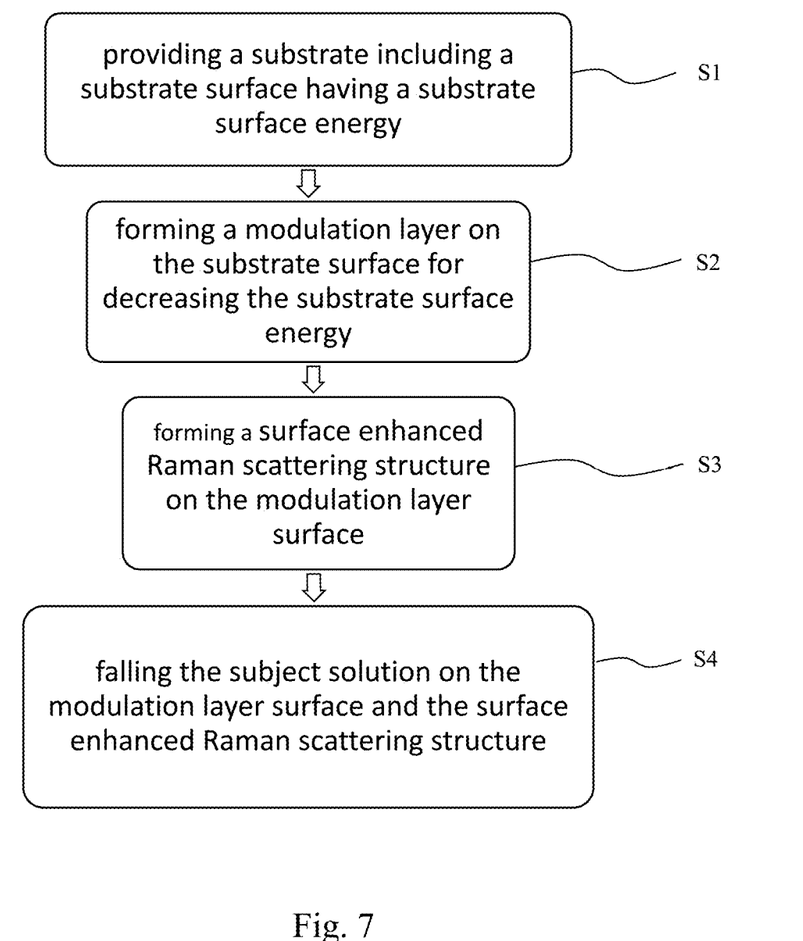
FIG. 7 is a flowchart of a method of manufacturing the surface enhanced Raman scattering device according to the invention.

FIG. 7 is a flowchart of a method of manufacturing the surface enhanced Raman scattering device 1 or 2 according to the invention. The method comprises the steps of: S1 providing a substrate 10 (or 20) including a substrate surface 101 (or 201) having a substrate surface energy; S2 forming a modulation layer 11 (or 21) on the substrate surface 101 (or 201) for decreasing the substrate surface energy in which the modulation layer 11 (or 21) includes a modulation layer surface 111 (or 211) having a modulation layer surface energy, and in which the modulation layer surface energy is less that the substrate surface energy; and S3 forming a surface enhanced Raman scattering structure 12 (or 22) on the modulation layer surface 111 (or 211).

In step S1, providing a substrate 10 (or 20) is not limited to filter paper. In step S2, forming a modulation layer 11 (or 21) on the substrate surface 101 (or 201) is not limited to: using PFOTS by carrying out vapor deposition in order to form the modulation layer 11 (or 21) on the substrate surface 101 (or 201) or using PFOTS to adjust the substrate surface energy of the substrate surface 101 (or 201). Further, the vapor deposition is, for example deposition.

In step S3, forming a surface enhanced Raman scattering structure 12 (or 22) on the modulation layer surface 111 (or 211) is carried out by, for example using a sputter deposition device to sputter a metal film on the modulation layer surface 111 (or 211) and optimizing an effective thickness of the metal film by controlling the sputtering time period. This is because attraction force among metal atoms of the metal nanoparticles is greater than that between the metal nanoparticles and the modulation layer surface 111 (or 211). The metal film forms a surface enhanced Raman scattering structure 12 (or 22) on the modulation layer surface 111 (or 211). The surface enhanced Raman scattering structure 12 (or 22) includes a plurality of discontinuously, densely arranged metal nanoparticles which in turn form a plurality of local electric field gain zones 122 (or 222). Further, thickness of the gold nano-film is controlled by adjusting the sputtering time period to 14, 20, 26, 32, or 38 second. Film Wizard is used to simulate the gold nano-film on a silicon substrate and results show an equivalent thickness of 3, 5, 7, 9, or 11 nm; an average diameter of particles of 22, 47, 54, 65, or 113 nm; and an average distance between particles of 17, 7, 13, 20, or 34 nm. The number of the gold nanoparticles increases and the particle size increases as the sputtering time in unit of second increases.

In other embodiments, chemical synthesis methods are used. In detail, citrate sodium as reducing agent, chloroauric acid as precursor of gold nanoparticles or silver nitrate as precursor of silver nanoparticles. Coating a solution having metal nanoparticles on the modulation layer surface 111 (or 211) forms a surface enhanced Raman scattering structure 12 (or 22). The metal nanoparticles are formed of a single kind of metal or different kinds of metal. The surface enhanced Raman scattering structure includes a plurality of discontinuously, densely arranged metal nanoparticles which in turn form a plurality of local electric field gain zones. In step S4, the subject solution 13 falls on the modulation layer surface 111 (or 211) and the surface enhanced Raman scattering structure 12 (or 22). The subject solution 13 includes the subjects 131 and the solvent 132. The subjects 131 are not limited to methylene blue (MB). The solvent 132 is not limited to water.

Figure 8:
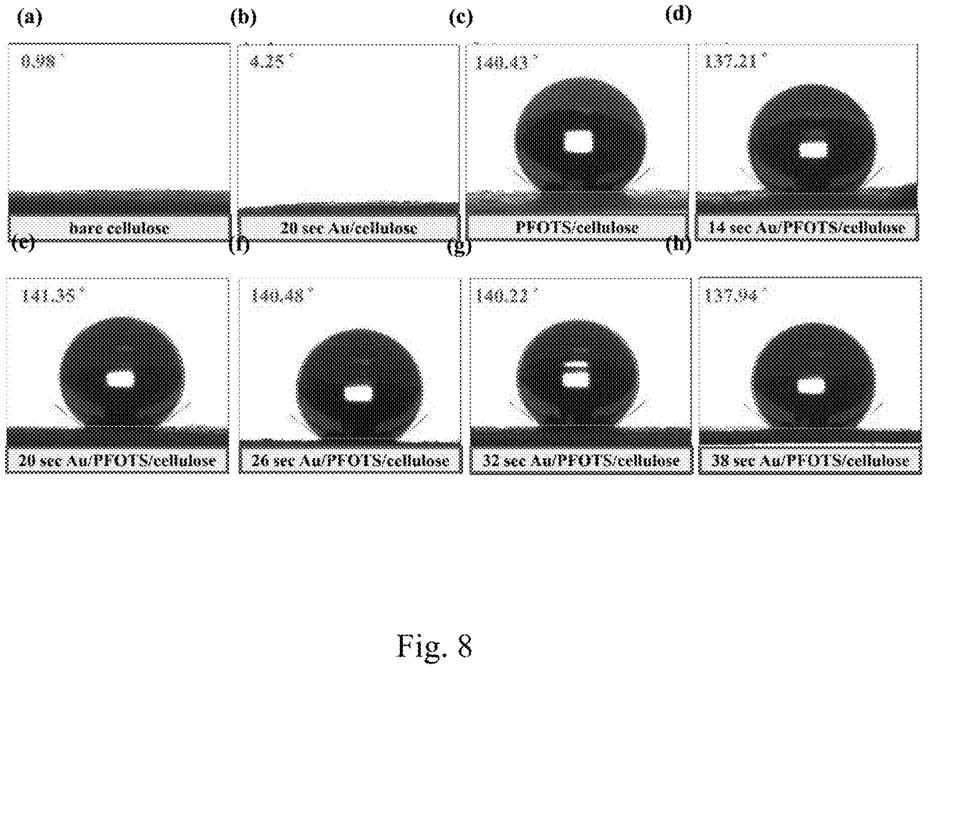
FIG. 8 are 8 images showing contact angles of falling the subject solution on the modulation layer surface and the surface enhanced Raman scattering structure using the modulation layer surface.

Referring to FIG. 8, in the embodiment of the invention there are 8 images showing contact angles of falling the subject solution 13 on the modulation layer surface 111 (or 211) and the surface enhanced Raman scattering structure 12 (or 22) using the modulation layer surface 111 (or 211). In detail, PFOTS is deposited on a filter paper and the deposited filter paper is hydrophobic. The contact angle is always about 140° with one sputtering lasted for a first time period (in the unit of second) which is different from another sputtering lasted for a second time period (in the unit of second). The hydrophobic nature of the sputtered filer paper is not affected as shown in parts (c) to (h) of FIG. 8.

In part (a) of FIG. 8, the original contact angle of the filter paper is 0.98°. After sputtering on a gold nano-film for 20 seconds, the contact angle of the filter paper changes to 4.25° as shown in part (b) of FIG. 8. As to the gold nano-film not being sputtered, PFOTS is deposited on the filter paper. The contact angle of the filter paper changes to 140.43° as shown in part (c) of FIG. 8.

Another method of manufacturing the surface enhanced Raman scattering device 3 according to the invention is characterized by comprising the steps of: providing a substrate 30 including a substrate surface 301 having a substrate surface energy; forming a modulation layer 31 on the substrate surface 301, the modulation layer 31 being for decreasing the substrate surface energy in which the modulation layer 31 includes a modulation layer surface 311 having a modulation layer surface energy which is less than the substrate surface energy; and forming a synthesized solution 33 on the modulation layer surface 311 in which the synthesized solution 33 includes a plurality of subjects 331, a solvent 332, and a plurality of metal nanoparticles 321 in which attraction force among molecules of the solvent 332 is greater than that between the solvent 332 and the modulation layer surface 311, and attraction force among metal atoms of the metal nanoparticles 321 is greater than that between the metal nanoparticles 321 and the modulation layer surface 111. The metal nanoparticles 321 are formed of a single kind of metal or different kinds of metal. Both the subjects 331 and the metal nanoparticles 321 concentrate on the condensation zone 34 after the solvent 332 has evaporated. A surface enhanced Raman scattering structure (not shown) is formed on the modulation layer surface 311 by the metal nanoparticles 321. Also, the subjects 331 are formed in the local electric field gain zones on the surface enhanced Raman scattering structure. The modulation layers 11, 21 and 31 have metal nanoparticles 121, 221 and 321 respectively in order to form densely arranged nanoparticles arrays.

The invention employs laser of 785 nm and 10 μL MB as subject. The sputtered gold nanoparticles are uniform in size. For 50 nm of the sputtered gold nanoparticles, it is possible of measuring a maximum enhanced Raman spectrum of $10^{-10}$ M MB with less noise. The surface enhanced Raman scattering substrate of the invention can be applied to food safety check, drug detection, environment pollution detection and clinical test. Currently, paraquat, amphetamine and creatinine can be detected by the invention. For paraquat, its concentration can be detected at a range of $10^{-5}$-10 mg/mL in which there are several significant Raman characteristic scattering peaks. The characteristic peak at 837 $cm^{-1}$ is vibration mode of carbon-nitrogen (C—N) bond, the characteristic peak at 1186 $cm^{-1}$ is vibration mode of carbon-carbon (C═C) double bond, the characteristic peak at 1292 $cm^{-1}$ is vibration mode of carbon-carbon (C—C)

single bond, and the characteristic peak at 1640 cm$^{-1}$ is vibration mode of (C=N) bond. For amphetamine and creatinine, 10$^{-6}$ mg/mL of amphetamine signal is detected in which there is a significant Raman characteristic peak at 1615 cm$^{-1}$ and it is vibration mode of C=C double bond. For 100 mg/mL of creatinine Raman signal, the most significant peak is 671 cm$^{-1}$ and it is vibration mode of C—N bond of benzene ring and vibration mode of carbon-oxygen (C=O) bond.

While the invention has been described in terms of preferred embodiments, those skilled in the art will recognize that the invention can be practiced with modifications within the spirit and scope of the appended claims.

What is claimed is:

1. A surface enhanced Raman scattering device, comprising:
    a first layer being a substrate including a first surface having a first surface energy;
    a second layer formed on the first surface and including a second surface having a second surface energy; and
    a surface enhanced Raman scattering structure formed on the second surface wherein the second surface energy is less than the first surface energy to result in hydrophobic condensation effect.

2. The surface enhanced Raman scattering device as claimed in claim 1, wherein the surface enhanced Raman scattering structure includes a plurality of discontinuously, densely arranged metal nanoparticles.

3. The surface enhanced Raman scattering device as claimed in claim 2, wherein attraction force among metal atoms of the metal nanoparticles is greater than that between the metal nanoparticles and the second surface.

4. The surface enhanced Raman scattering device as claimed in claim 1, wherein the surface enhanced Raman scattering structure includes a plurality of local electric field gain zones, the local electric field gain zones being on the second surface.

5. The surface enhanced Raman scattering device as claimed in claim 4, wherein local electric field gains of the local electric field gain zones are not the same.

6. The surface enhanced Raman scattering device as claimed in claim 4, further comprising a subject solution including a plurality of subjects and a solvent, the subject solution being on both the second surface and the surface enhanced Raman scattering structure, and wherein attraction force among molecules of the solvent is greater than that between the solvent and the second surface so when the subject solution falls on the second surface having a lower surface energy, a spatial distribution range of the subject is decreased to a minimum as the solvent evaporates; thus, only a few amount of the subjects is needed to achieve stronger Raman measurement signals and a purpose of testing a trivial subject.

7. The surface enhanced Raman scattering device as claimed in claim 4, further comprising a plurality of subjects in the local electric field gain zones.

8. The surface enhanced Raman scattering device as claimed in claim 1, wherein both the first surface and the second surface are a three-dimensional structure.

9. A surface enhanced Raman scattering device, comprising:
    a first layer being a substrate including a first surface having a first surface energy;
    a second layer formed on the first surface and including a second surface having a second surface energy wherein the second surface energy is less than the first surface energy to result in hydrophobic condensation effect; and
    a synthesized solution on the second surface, the synthesized solution including a plurality of subjects, a solvent, and a plurality of metal nanoparticles wherein attraction force among molecules of the solvent is greater than that between the solvent and the second surface so when the subject solution falls on the second surface having a lower surface energy, a spatial distribution range of the subject is decreased to a minimum as the solvent evaporates; thus, only a few amount of the subjects is needed to achieve stronger Raman measurement signals and a purpose of testing a trivial subject.

10. A method of manufacturing a surface enhanced Raman scattering device, comprising the steps of:
    providing a first layer being a substrate including a first surface having a first surface energy; and
    forming a second layer on the first surface, the second layer including a second surface having a second surface energy wherein the second surface energy is less that the first surface energy to result in hydrophobic condensation effect.

11. The method of manufacturing a surface enhanced Raman scattering device as claimed in claim 10, wherein the second layer is formed on the first surface by means of vapor deposition.

12. The method of manufacturing a surface enhanced Raman scattering device as claimed in claim 11, further comprising the step of forming a surface enhanced Raman scattering structure on the second surface by sputtering, the surface enhanced Raman scattering structure including a plurality of discontinuously, densely arranged metal nanoparticles which form a plurality of local electric field gain zones.

13. The method of manufacturing a surface enhanced Raman scattering device as claimed in claim 12, further comprising the steps of providing a subject solution including a plurality of subjects and a solvent, coating the subject solution on both the surface enhanced Raman scattering structure and the second surface, and evaporating the solvent to leave the subjects in the local electric field gain zones, wherein attraction force among molecules of the solvent is greater than that between the solvent and the modulation layer second surface so when the subject solution falls on the second surface having a lower surface energy, a spatial distribution range of the subject is decreased to a minimum as the solvent evaporates; thus, only a few amount of the subjects is needed to achieve stronger Raman measurement signals and a purpose of testing a trivial subject.

14. The method of manufacturing a surface enhanced Raman scattering device as claimed in claim 11, wherein further comprising the step of forming a surface enhanced Raman scattering structure on the second surface by coating a solution having a plurality of dispersed metal nanoparticles on the second surface, the surface enhanced Raman scattering structure including a plurality of discontinuously, densely arranged metal nanoparticles which form a plurality of local electric field gain zones.

15. The method of manufacturing a surface enhanced Raman scattering device as claimed in claim 14, wherein the metal nanoparticles include a metal precursor and a reducing agent.

16. The method of manufacturing a surface enhanced Raman scattering device as claimed in claim 14, further comprising the steps of providing a subject solution including a plurality of subjects and a solvent, coating the subject solution on both the surface enhanced Raman scattering structure and the second surface, and evaporating the solvent to leave the subjects in the local electric field gain zones, wherein attraction force among molecules of the solvent is greater than that between the solvent and the modulation layer second surface so when the subject solution falls on the second surface having a lower surface energy, a spatial distribution range of the subject is decreased to a minimum as the solvent evaporates; thus, only a few amount of the subjects is needed to achieve stronger Raman measurement signals and a purpose of testing a trivial subject.

17. The method of manufacturing a surface enhanced Raman scattering device as claimed in claim 11, further comprising the steps of providing a synthesized solution including a plurality of subjects, a solvent, and a plurality of metal nanoparticles, coating the synthesized solution on the second surface, and concentrating the metal nanoparticles to form a surface enhanced Raman scattering structure by evaporating the solvent wherein the surface enhanced Raman scattering structure includes a plurality of discontinuously, densely arranged metal nanoparticles which form a plurality of local electric field gain zones, and the subjects are in the local electric field gain zones, wherein attraction force among molecules of the solvent is greater than that between the solvent and the modulation layer second surface so when the subject solution falls on the second surface having a lower surface energy, a spatial distribution range of the subject is decreased to a minimum as the solvent evaporates; thus, only a few amount of the subjects is needed to achieve stronger Raman measurement signals and a purpose of testing a trivial subject.

* * * * *